United States Patent [19]

Begg et al.

[11] Patent Number: 5,516,698

[45] Date of Patent: May 14, 1996

[54] METHODS AND APPARATUS ALLOWING SEQUENTIAL CHEMICAL REACTIONS

[75] Inventors: Geoffrey S. Begg, Heidelberg; Richard J. Simpson, Richmond; Antony W. Burgess, Camberwell, all of Australia

[73] Assignee: Ludwig Institute For Cancer Research, N.Y.

[21] Appl. No.: 842,363

[22] PCT Filed: Apr. 11, 1991

[86] PCT No.: PCT/AU91/00141

§ 371 Date: Apr. 30, 1992

§ 102(e) Date: Apr. 30, 1992

[87] PCT Pub. No.: WO91/15758

PCT Pub. Date: Oct. 17, 1991

[30] Foreign Application Priority Data

Apr. 11, 1990 [AU] Australia ................................. 9605/90

[51] Int. Cl.[6] ........................ G01N 27/30; G01N 27/447
[52] U.S. Cl. ........................... 436/89; 436/180; 204/450; 204/451; 204/452
[58] Field of Search ............................... 436/86–90, 149, 436/150, 151, 161, 173, 175, 177, 178, 180; 422/101, 82.01, 82.02, 186.04, 67; 204/299 R, 302, 180.1, 186

[56] References Cited

U.S. PATENT DOCUMENTS

| | | |
|---|---|---|
| 3,338,812 | 8/1967 | Dworak et al. . |
| 3,717,436 | 2/1973 | Penhasi et al. . |
| 3,725,010 | 4/1973 | Penhast . |
| 4,065,412 | 12/1977 | Dreyer . |
| 4,155,714 | 5/1979 | Bonner et al. . |
| 4,603,114 | 7/1986 | Hood et al. . |
| 4,610,847 | 9/1986 | Hood et al. . |
| 4,665,037 | 5/1987 | Stolowitz . |
| 4,704,256 | 11/1987 | Hood et al. . |
| 4,820,648 | 4/1989 | Caprioli et al. ........................... 436/89 |
| 4,863,870 | 9/1989 | Stolowitz et al. ........................ 436/89 |
| 5,057,438 | 10/1991 | Imai et al. ............................... 436/516 |
| 5,151,165 | 9/1992 | Huynh ................................. 204/299 R |

FOREIGN PATENT DOCUMENTS

| | | |
|---|---|---|
| 0395319 | 10/1990 | European Pat. Off. . |
| 1019893 | 5/1962 | United Kingdom . |
| 1229890 | 6/1969 | United Kingdom . |

*Primary Examiner*—Jeffrey R. Snay
*Attorney, Agent, or Firm*—Felfe & Lynch

[57] ABSTRACT

A first reactant is immobilized i.e. in a porous matrix (50), adjacent a sample electrode (46) within a reaction chamber. Energizing of the electrode (46) electrophoretically attracts a mobile second reactant and/or electrolytically induces appropriate reaction conditions to enhance reaction of the first and second reactants. Polarity reversals between the sample electrode (46) and remote electrodes (38), (42), (44) cause unreacted second reactant and/or by-products to migrate away from the immobilized first reactant. The techniques are useful for sequential chemical reactions such as sequencing or construction of proteins, polysaccharides and nucleic acids where cyclical additions and removals of reactants are required. The techniques are amenable to automated micro and nano scale construction and operation and allow direct electrophoretic (38) interfacing with chromatographic, HPCE and mass spectrophotometric equipment.

4 Claims, 5 Drawing Sheets

METHODS AND APPARATUS ALLOWING SEQUENTIAL CHEMICAL REACTIONS

This invention relates to methods and apparatus for carrying out chemical reactions between a plurality of reactants and in particular it is amenable to micro or nano scale operation and to the sequential chemical reactions required during such processes as construction or sequencing of proteins, oligonucleotides and polysaccharides.

A classic example of a sequential chemical reaction is the Edman protein sequencing technique involving the stepwise removal and identification of the N-terminal amino acid residues of a protein. The traditional Edman technique involves coupling the N-terminal amino acid residue to phenylisothiocyanate (PITC) in a solvent under alkaline or anhydrous conditions to form a phenylthiocarbamyl derivative. Excess PITC (usually at least 100 fold molar excess) is removed, typically by liquid extraction and the solvent also removed. The N-terminal amino acid, coupled to the PITC is subjected to cleavage by anhydrous acid to form an anilinothiazolinone (ATZ) derivative of the amino acid. The ATZ derivative is removed for subsequent chromatographic identification of the amino acid portion. The original protein is thus truncated, at its N-terminal by one amino acid allowing access to the formerly penultimate amino acid to be coupled, cleaved and identified with a subsequent Edman cycle. Further cycles can be undertaken to determine the entire sequence of the protein.

Some of the disadvantages of the traditional liquid phase Edman technique include the necessity to introduce plural incompatible reagents to achieve the coupling and cleavage steps for each cycle. In particular it is noted that strong alkali conditions are required in the coupling step whereas a strong acid environment achieves the cleavage. Clearly differentiation of these strong reagents is required to ensure a consistent removal of all the N-terminal residues without also generating spurious derivatives or uncoupling further non terminal residues. Furthermore the requirement for removal of the various volatile and non volatile auxiliary reagents and solvents during each cycle leads to sample loss and/or the formation of insoluble by-products. Relatively large volumes of sample and reagents are also required.

Effective automation of the Edman technique is first described in Edman and Begg, "A Protein Sequenator", in the European J. Biochem. 1, (1967), 80–91 and in U.S. Pat. No. 3,725,010. In these sequenators a liquid phase Edman technique is carried out in a thin film formed on the inside wall of a rotating reaction cell, now termed a "spinning cup". The spinning cup is located within a closed reaction chamber to maintain an inert atmosphere. Reagents are added to the cup by a system of pumps and valves and material removed by overflow over the lip of the spinning cup, vacuum evaporation or by dissolving or extracting in non polar solvents. The liquid reagents and solvents themselves form films on the walls of the spinning cup which pass over and interact with the sample film as the cup spins. The reagents dissolve the sample film and perform the coupling and cleavage stages of the Edman process, after which volatiles are removed by evacuation and the remaining sample film solvent extracted to transfer resulting amino acid thiazolone for identification.

It will be apparent that this dynamic system, requiring fluid and vacuum seals is difficult to construct and operate. The agitation induced by the spinning cup can cause the sample film to be overly extracted during washing or dislodged, in particular if the small protein being sequenced is a polypeptide. The initial protein sample must therefore be relatively large in volume and chain length. The drying of the protein onto the inner wall of the spinning cup must also be performed very carefully and slowly to achieve an even thin film while avoiding boiling and splatter during desiccation. Precise metering of reagents and solvents into the cup is also required to ensure consistency between cycles.

Laursen, in the European J. Biochem. 20 (1971), and Waschter et al., FEBS LeH 35, 97 (1973), described alternative automatic sequencers in which the sample is immobilized by covalent linkage to the surface of a bead matrix/gel type solid phase. This allows all reagents and solvents to be removed by solvent replacement rather than vacuum evaporation or other drying. Solvent replacement techniques, however, necessitate covalent linkage of the sample to avoid washout by the solvents used. U.S. Pat. Nos. 4,704,256, 4,610,847 and 4,603,114 relate to similar technologies in which the sample is embedded in a permeable matrix and subject to liquid solvents.

Drawbacks of the solvent systems as discussed above have led to gas solid phase Edman techniques, for instance as described in U.S. Pat. Nos. 3,892,531 and 4,065,412. In the former patent the sample is attached to a finger like extension within a reaction chamber, while the latter applies the sample to inner and outer surfaces of macroporous beads. In each system at least one of the reagents is introduced in the gaseous form; however neither system is amenable to contamination free, multiple cycles due to inefficiencies in washing by dew formation on the finger or by channelling of the solvent between rather than through the beads.

Each of the above mentioned sequenators have required undesirably large samples due to various inefficiencies in washing etc. British Application No. GB 2146550 describes an attempt to miniaturize a reaction flask suitable for Edman technique having capillary tubes to spray wash interior walls bearing an immobilizing sample matrix. Fluids within the flask can be agitated by the introduction of a gaseous phase. There is still, however, a need for systems more amenable to miniaturization and using even smaller samples. There is also a need for systems allowing direct interfacing of the chemical reactor with identification or assay apparatus such as mass spectrometers, chromatographs etc.

The above described Edman technique for terminal degradation of a protein, successively removed N-terminal residues. Alternative systems using a C-terminal degradation, such as phosphoryl mercaptobenzothiazole or benzoyl isothiocyanate are described in "Methods in Protein Sequence Analysis" (1991) Jörnvall/Höög/— Gustavsson (Eds) Birkhäuser Verlag, Basel. The latter system embodies a two stage couple/cleave reaction between the cleaving reagent and C-terminal amino acid, rather like the Edman technique. Further guidance on protein sequencing is founding in Schlack et al. (1926) Hoppe-Seylers, Z. Physiol. Chemie., 154, 126–170 and Stark (1972) "Methods in Enzymology", Hirs/Timascheff (Eds) Academic Press, 25, 369.

The above description of previous techniques and apparatus has centred on protein sequencing, but it will be readily apparent that many other chemical processes face similar problems of sample loss or contamination, inefficient or overly vigorous washing, inefficient access of reagents etc. Examples of such reactions includes site specific modification, construction or sequencing of other macromolecules.

In accordance with a first aspect of the present invention there is provided a method of conducting a chemical reaction, the method comprising immobilizing a first reactant at a reaction locus, electrophoretically introducing to the reaction locus at least one charged, additional reactant and after reaction between the first and additional reactants removing the remaining additional reactant and/or a reaction by-product of the reaction from the reaction locus.

A related aspect of the invention provides chemical reaction apparatus, comprising a reaction locus, immobilizing means for securing a first reactant at the reaction locus, means for the electrophoretic introduction to the reaction locus of at least one additional reactant and means to remove, from the locus, the remaining additional reactant and/or a reaction by-product of the first and additional reactants.

By the use of the present invention the electrophoretic introduction of the additional reactant causes it to focus or concentrate around the electrode upon which is immobilized the first reagent. Thus a relatively dilute concentration of the additional reactant can achieve enhanced concentrations and therefore reaction efficiencies. Comparatively weak feed solutions of the additional reactant have the advantage of facilitating washing out thereof prior to subsequent reactant additions, thereby minimizing contaminating carry-over.

In the context of this specification "chemical reactions" is being used in its classical sense denoting a molecular level interaction between the first and additional reactants resulting in a change in structure of one or both reactants and includes such interactions as enzymatic reactions. Furthermore, "electrophoretic" includes "electrokinetic".

The first reactant will typically be immobilized immediately adjacent an electrode serving to cause electrophoretic migration of the charged additional reactant. Preferably the first reactant is immobilized on such an electrode itself or on a sample matrix extension thereof.

At its simplest, the above mentioned means to remove remaining additional reactant and/or reactant by-product flush these materials away from the reaction locus. Suitably controlled syringes or pumps can be used to achieve this. The method and apparatus of this aspect of the invention may however be adapted to the collection and/or identification of a reaction by-product of the first and an additional reactant. A convenient arrangement where the by-product is itself charged or can be made charged provides electrophoretic or electrokinetic means to selectively remove the by-product for subsequent analysis away from the reaction locus by, for instance, mass spectrometry or capillary electrophoresis. These analytical techniques use extremely small samples. As the apparatus and method of the invention are amenable to micro and nano scale reactions, direct injection of the by-product described above into the sample port of the analysis instrument becomes possible thus minimizing losses and inaccuracies which may occur, for instance, during sample dilution in prior art methods. Other appropriate analysis equipment may involve electromagnetic absorption, fluorescence, nuclear resonance, immunological detection, gas liquid chromatography GLC etc.

The above mentioned arrangement having electrophoretic removal of reaction by-products is not necessarily limited to a set-up in which the additional reactant(s) is/are introduced electrophoretically.

Accordingly, a second aspect of the invention provides a method of conducting a chemical reaction, the method comprising immobilizing a first reactant at a reaction locus, introducing an additional reactant to the reaction locus, allowing a reaction between the first and additional reactants to produce a reaction by-product, if the reaction by-product is not charged, imparting an electrical charge to the reaction by-product and electrophoretically removing, from the reaction locus, the by-product for collection or analysis. Conveniently this electrophoretic removal directly injects the by-product into an analysis instrument as described immediately above.

A related aspect of the invention provides apparatus for conducting a chemical reaction, the apparatus comprising a reaction locus, immobilizing means for securing a first reactant at the reaction locus, means to introduce an additional reactant to the reaction locus, optionally means to impart a charge to a reaction by-product of a reaction between the first and additional by-products and means to electrophoretically remove from the reaction locus, the reaction by-product.

Conveniently an ion exchange membrane intermediate the reaction locus and the injection port is used to separate the by-product from other species in the reaction portion of the apparatus. Ion exchange membranes such as BIO-REX products having AG ion exchange resin beads permanently enmeshed in a polyfluoroethylene matrix are available with a number of ion exchange varieties suitable for separating different species of by-products, both cationic and anionic.

Where a reaction by-product is directly injected into the sample port of an analysis apparatus, electrophoretically or otherwise, it is desirable to employ a phase contrast between the reaction locus medium and the analysis medium. For instance where the medium around the reaction locus comprises a non polar medium, a polar medium in the sample injection port of the analysis apparatus in conjunction with a suitable hydrophobic membrane can assist in separating the by-product from the reaction solvent or diluent. An example can be taken from the above noted Edman technique which utilises an organic medium. In contrast a capillary electrophoresis analyser can run on an aqueous medium. Separation of the by-product is efficiently achieved through a hydrophobic reaction locus medium by a porous hydrophobic membrane composed of polytetrafluoroethylene. Conversely in other reaction systems an aqueous reaction medium around the reaction locus may encourage the use of non polar chromatographic detection techniques in conjunction with porous hydrophilic membranes.

The methods and apparatus defined above may be particularly suited to sequential chemical reactions between the first reactant and a plurality of individual second and subsequent reactants. Thus a first reaction may be commenced by electrophoretically introducing a second reactant to the first reactant following which unreacted second reactant and reaction by-products can be flushed away or electrophoretically removed. Thereafter a third reactant may be (electrophoretically) introduced to the reaction locus for reaction with an immobilized reaction product of the first and second reactants. In this way an ordered sequence of reaction products, as may be used in the construction of macromolecules such as polysaccharides, oligonucleotides or proteins may be built up on the immobilized first reactant. It will of course be necessary to provide such additional reactant "building blocks" with a suitable charge to ensure their electrophoretic migration to the "foundation" first reactant. It will also be necessary, if a macromolecule having an ordered sequence is to be built up, to ensure that the additional reactant bonds at the desired terminal of the incipient macromolecule. To this end appropriate capping enzymes (such as glycosyl transferases for polysaccharides or ribosomal transferases for proteins) can be introduced into the reaction medium. Alternatively acid or base catalysed condensations can be enhanced by in situ acid/base generation as described later.

Alternative sequential chemical reactions occur in protein, oligonucleotide or polysaccharide sequencing. The prior art discussion above in relation to the Edman technique or C-terminal degradation of a protein is an example of such sequencing reactions. When the present invention is applied to such sequencing reactions, the first reactant can comprise the protein, oligonucleotide or polysaccharide to be sequenced, while the additional reactant may comprise a cleaving agent, successive aliquots of which can be introduced to the macromolecule first reactant. The cleaved off by-product i.e. amino acid, nucleic acid or saccharide, can be collected for analysis after the reaction of the macromolecule with each aliquot of cleaving agent and before the next aliquot of cleaving agent is introduced to the immobilized macromolecule. By appropriate choice of charge for the respective reactants and by-products, the additional reactant and/or by-product of the reaction can be electrophoretically separated for subsequent analysis of the by-product and/or collection of unreacted additional reactant for reuse or discard.

Furthermore, if unreacted additional reactant is electrophoretically removed from the reaction locus and collected at a collection locus adjacent a collection electrode it is possible, by reversing the respective voltages of collection and reaction locus electrodes, to cause a second aliquot of the additional reactant for instance a cleaving reagent in a sequencing system to be reintroduced to the reaction locus from the collection locus. The collection locus thus operates as a reservoir for the additional reactant.

Alternative reactions involving macromolecules and amenable to the present invention include the immobilizing of an enzyme such as a restriction endonuclease or endopeptidase to allow analysis of the nucleotide or polypeptide structure not requiring end terminal truncation. Conversely a peptide or nucleic acid of interest could be immobilized and subsequently introduced to a series of peptidase or nucleases to determine cleavage pattern. Such an approach is useful in determining, eg. if fusion proteins have been produced by a recombinant host or in DNA restriction analysis.

It is also contemplated that the structure of macromolecules other than proteins, polysaccharides and nucleotides such as long chain lipids, glycoproteins and glycolipids could be determined using techniques of the invention, typically utilizing enzymic cleavage.

A useful feature forming a third aspect of the invention but also observed in the above described electrophoretic apparatus and methods is that energizing of an electrode having the first reactant attached thereto can electroactivate reagents in the medium nearby. For instance a negatively charged electrode will attract positively charged reactants. Additionally it can electrolyse, to some extent, reagents or solvents nearby or in some circumstances the first reactant. Such electrolysis can assist in activation of certain reactions or provide acid or base conditions immediately adjacent the electrode. For instance in the earlier discussed classic Edman technique, a base environment is required to react the Edman reagent i.e. the isothiocyanate coupling agent to the N-terminal amino acid. Traditionally the base conditions are provided by adding a strong base such as Quadrol (Wyandotte Chemicals Corp.) buffer to the reaction vessel. It has now been discovered, however, that basic conditions can be generated in situ adjacent the sample by electrolysis following energizing of the electrode bearing the first reagent. Similarly acid conditions required, for instance, in the cleavage step of Edman procedures can be generated in situ by positive charge energizing of the electrode. It should be noted that this aspect of the invention is not limited to electrophoretically transferred reagents as non charged Edman reagents such as PITC can also be "electroactivated" by basic conditions produced by a negatively charged electrode.

Accordingly a third aspect of the invention provides a method of conducting a chemical reaction, the method comprising immobilizing a first reactant at an electrode defining a reaction locus, introducing at least one additional reactant to the reaction locus, electrolytically activating a reaction between the first and additional reactants by energizing the electrode and thereafter removing from the reaction locus, remaining additional reactant and/or a reaction by-product of the reaction.

Further provided by this invention and related to this third aspect, is chemical reaction apparatus comprising an electrode defining a reaction locus, means to immobilize a first reactant at the reaction locus, means to introduce an additional reactant to the reaction locus, means to energize the electrode thereby electrolytically activating a reaction between the first and additional reactants and means to remove from the reaction locus remaining additional reactant and/or a reaction by-product of the reaction.

With this aspect of the invention, the electroactivation of the reaction between first and additional reactants can either be by in situ generation of appropriate pH conditions to enhance reaction kinetics (as with the Edman technique example described immediately above). It will also be apparent that in alternative reaction systems active radicals can be formed in situ, adjacent the electrodes by direct electrolysis of the first or more usually the additional reactant.

Electrolysis to produce electroactivated species will occur most efficiently where the field strength is strongest. It is thus desirable to immobilize the first reactant immediately adjacent a conductor such as a platinum, such that the electric field strength through the first reactant is maximized. In effect a sample matrix immobilizing the first reactant becomes an extension of the electrode itself.

Referring still to the "electroactivating" aspect of the invention, as with the earlier described first aspect of the invention, the means to remove the remaining additional reactant and/or reaction by-product may simply comprise a pump or syringe to flush the reaction locus. Preferably however, the method and apparatus allow the collection and/or identification of a reaction by-product. As described above electrophoretic means can be provided to selectively remove the by-product, if it is charged, for subsequent analysis away from the reaction locus. Where a by-product does not inherently bear a charge, introduction of charged surfactants, such as SDS sodium dodecyl sulphate can render such materials electrophoretically migratable.

It will be apparent that each of the above described aspects of the invention are amenable to micro and nano scale construction and operation. Reaction locus volumes of less than $1 \times 10^6$ nl, preferably $1 \times 10^3$ nl and even of the order of 10 nl to 100 nl are achievable and desirable. Correspondingly small ampages of electrolytic or electrophoretic current, of the order of fractions of a milliamp—for instance 0.01 to 10 µA can be used. Low currents assist in preventing temperature surges in the cell. This has many advantages over current more macro scale techniques in macromolecular construction and sequencing. It allows the use of extremely small amounts of the reactant immobilized at the reaction locus. This is particularly important in sequencing work where the nucleotide, protein or polysaccharide may not be available in large quantities or, as has been discovered during the use of prior art techniques discussed above, may be difficult to manipulate in small quantities. As mentioned above a micro or nano scale operation allows direct injection of reaction by-products (i.e. cleavage residues) into highly sensitive analysis apparatus without requiring dilution or other preparation steps.

Referring still to the advantages of micro or nano scale operation, difficulties in effectively washing the reaction locus without disturbing the immobilized reagent, a particular problem in many prior art techniques, is lessened in the present invention where comparatively small amounts of reagents, diluents and washes can be used. In this regard it will be recalled that in the electrophoretic aspect of the invention, comparative weak reagent concentrations, can be tolerated due to the electrophoretic focussing of the active reagent at the reaction site. Weakly concentrated reagents are of course more easily removed and washed away than more concentrated solutions known in the prior art. Additionally, or alternatively, in the electrolytic aspect of the invention, electroactivation in situ of reagents can allow the use of less concentrated reagent feedstock, and/or eliminate the need to add strong pH control agents. Again the effect of this is to facilitate removal of unwanted reagents and by-products thus preventing carry-over and contamination of subsequent reactions at the reaction locus.

With any of the above defined aspects of the invention, immobilization of the first reactant, typically on an electrode is required. Several of the prior art techniques discussed above have immobilized proteins via covalent linkages. Securing the reagent strongly was important to prevent loss of the sample during the various reactions and washings but is difficult to achieve without adversely affecting the reagent. In contrast the present invention allows gentler methods of attachment of the first reagent at the reaction locus. Desirably the first reagent can be adsorbed directly onto a porous matrix which allows access of the additional reagents to the first reactant particularly its end terminals. Many such matrices are known for polysaccharides, proteins and nucleotides. Examples of such matrices include PVDF, nitrocellulose, glass, quartz, activated glass, activated quartz, cellulose, derivatized cellulose, nylon, plastic or activated plastic. Adsorption in this fashion, unlike covalent binding assists in preserving the structure of the first reagent which is particularly important in sequencing and macromolecule construction operations.

Reaction kinetics will, of course, differ between different combinations of reactants. In the case of a sequential chemical reaction, such as terminal degradation sequencing each residue along the chain may have differing kinetics of reaction with a cleavage reagent. Proline, for instance, in Edman degradation techniques requires a longer reaction time to achieve complete coupling than other amino acids. It is thus desirable to be able to monitor extent of reaction within the cell. This can be achieved colorimetrically by utilizing redox indicators which change colour or absorbance as the redox potential at the reaction locus changes. Other spectrophotometric techniques including laser induced fluorescence are also available which have the advantage of not requiring additional reagents at the reaction locus. Alternatively the extent of reaction can be measured amperometrically by monitoring current through an electrode defining the reaction locus. Thus a plateauing of electrolytic activation can be used to indicate completion of a coupling or cleavage reagent.

Various embodiments of apparatus and methods in accordance with the invention will now be described by way of example only with reference to the following Examples and to the accompanying drawings in which.

These embodiments of apparatus and methods will be described with reference to protein sequencing by the Edman sequential degradation process. In short, this application of the invention involves immobilizing a protein sample on an electrode at a reaction locus, for instance, within a glass electrophoresis chamber. A first aliquot of a cleaving agent is caused to electrophoretically migrate to the reaction locus to cleave an end amino acid from the immobilized protein. The cleaved amino acid molecules are then electrophoretically transferred to an analysis apparatus, in this case high performance capillary electrophoresis apparatus for identification thereof. Subsequently, second and further aliquots of the cleaving agent can be electrophoretically introduced to the reaction locus to sequentially cleave the remaining amino acids and thus allow the sequence to be determined. The achievement of this method wall be discussed in further detail below.

Figure 1:
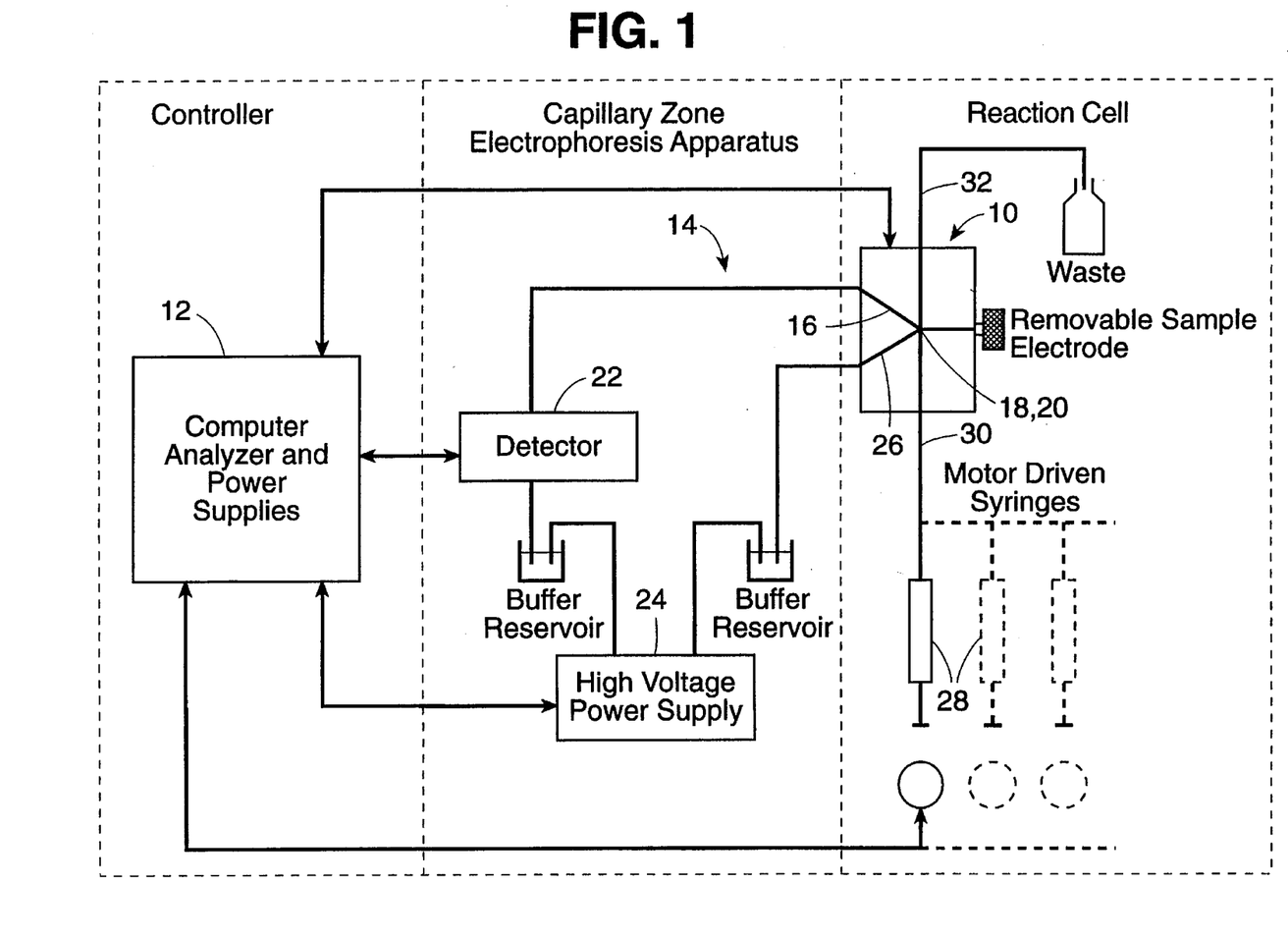
FIG. 1 is a schematic plan of a first embodiment of the reaction apparatus in conjunction with ancillary analysis and control equipment.

Referring initially to FIG. 1, the reaction apparatus 10 is depicted in conjunction with ancillary computer control device 12 and amino acid analysis apparatus 14 in the form of a capillary zone electrophoresis (HPCE) apparatus of known construction (see for instance Gordon, M. J. et al. (1988) "Capillary Electrophoresis Science", (242):242–248).

In short, the HPCE performs electrophoresis of very small quantities (5–50 nL) within capillary tubing typically of $\leq 100$ μm i.d. In the schematically depicted apparatus 14, the electrophoretic separation column 16 has its sample injection port 18 opening directly into a reaction chamber 20 of the reaction apparatus 10. This arrangement is described in detail below with reference to FIG. 2. The remaining major functions of the HPCE are a detector 22 monitoring the separated species from the column 16, and a high voltage source 24 in communication with the injection port 18 and column 16 through buffer line 26.

The reaction apparatus 10, in addition to the above mentioned reaction chamber 20 includes a plurality of cleavage reactant and flushing agent syringes 28 leading into the chamber 20 via inflow line 30. Leading from the chamber 20 is outflow 32 to waste.

A plurality of electrodes (not depicted in FIG. 1) each with a respective lead, are disposed within the reaction chamber. Each electrode is independently under the control of the computer 12, as are the syringes 28 enabling the method of the invention to be automated. The computer 12 further receives data from the detector 22 of the HPCE 14.

Figure 2:
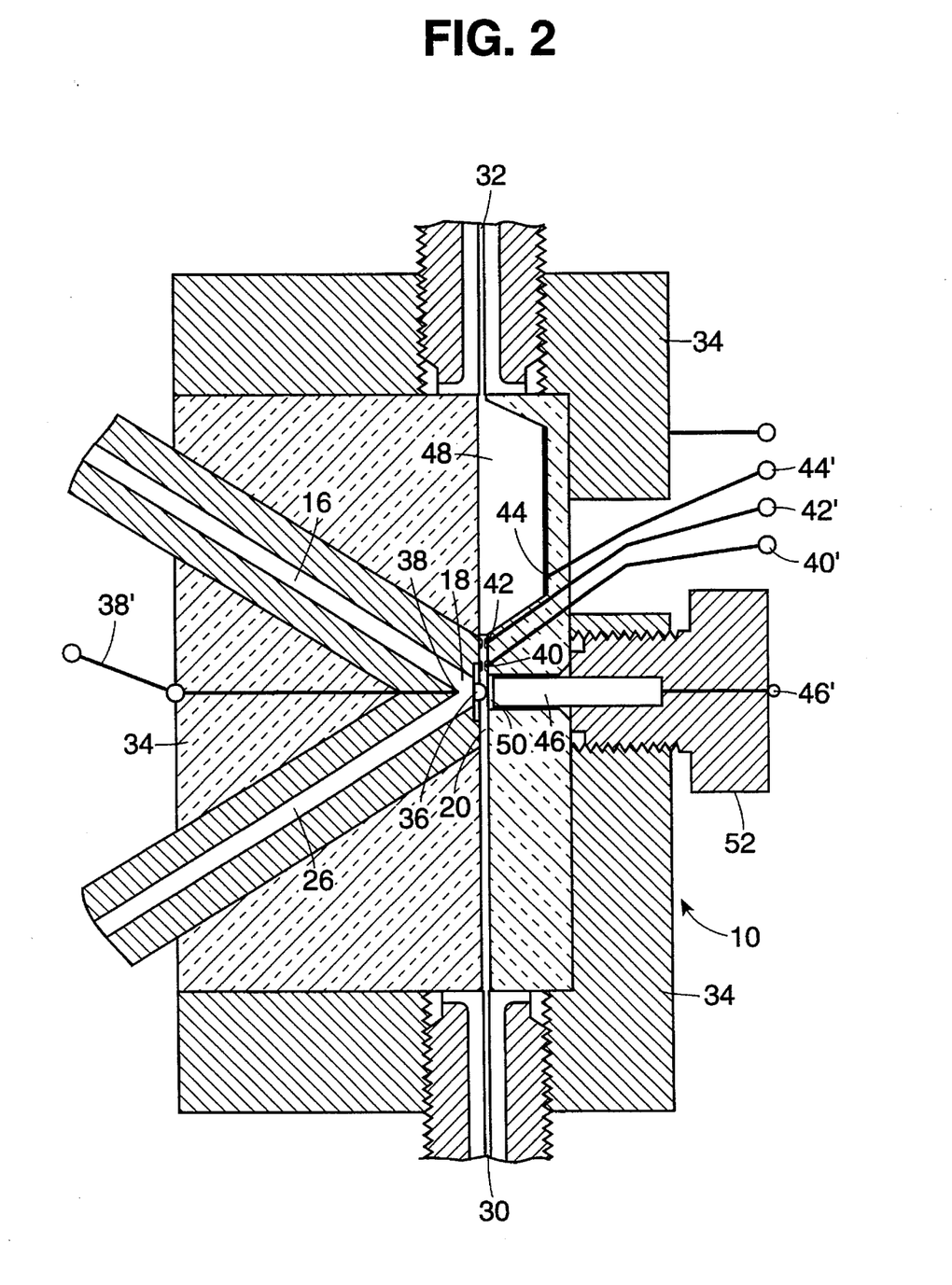
FIG. 2 is a sectional side view of the reaction apparatus of FIG. 1.

Turning now to FIG. 2, the reaction apparatus 10 comprises the electrophoretic reaction chamber 20 defined between a plurality of closely fitted and secured glass blocks 34. Clearly, other inert materials such as glass, quartz, ceramic, plastics etc. may be employed for the construction of a suitable chamber within which to conduct the electrophoretic transfers required by the invention. Conveniently, at least a portion of the material defining the chamber is transparent to allow the use of optical monitoring equipment such as an absorbance spectrophotometer to gauge the progress of reactions at the reaction locus and/or monitor the transfer of reactants or by-products to or from the locus. Advantageously, the material defining the chamber allows the temperature of the contents of the chamber to be kept steady. This may be achieved by an active heat transfer system such as a peltier device.

As mentioned above, leading into the reaction chamber 20, but separated therefrom by a hydrophobic porous PTFE membrane 36 is the sample injection port 18, buffer line 26 and capillary column 16 of the HPCE. An electrode 38 is mounted within the injection port. For simplicity, the electric lead 38' connecting the electrode 38 to the voltage source/ computer 12 has been truncated.

Three further electrodes, 40, 42 and 44 are disposed on an interior wall of the reaction chamber 20 successively downstream of a sample electrode 46 disposed facing the membrane 36 over the HPCE injection port. Each of the electrodes 40, 42, 44 and 46 has a respective lead 40', 42', 44' or 46' which have also been truncated for clarity but lead to the computer 12 for adjustment of respective voltages applied between the various electrodes. Electrode 44, most remote from the sample electrode 46 is disposed on an interior wall portion of an expanded portion 48 of the reaction chamber defining an electrophoretic storage locus as described further below.

When fitted, the sample electrode 46 terminates, within the reaction chamber, at a chemically inert protein immobilizing matrix 50 such as a polyvinylidene difluoride porous membrane. The sample electrode 46 further comprises a removable threaded support 52 to disengageably secure the electrode through the chamber walls. The sample electrode in this embodiment is platinum but other electrically conductive materials such as gold, tungsten or graphite may also be appropriate.

The apparatus is adapted to miniaturization enabling fine temperature and environmental control thereby to optimize the sequential degradation process. The reaction chamber may be, for instance, of the order of a millimeter or significantly less across allowing the use of very low ($\mu$A) currents for the electrophoretic transfers. This further assists in preventing temperature surges which may effect the chemical reaction.

Sample loading

In use, the sample (for example, protein or oligopeptide) is immobilized by application, external to the apparatus, to the chemically inert immobilizing matrix (e.g. porous polyvinylidene difluoride (PVDF) membrane 50) affixed to the end of the removable, insulated (PTFE) platinum electrode 46 either by passive means (e.g. direct spotting) or electrotransfer. After sample immobilization, sample electrode 46 is reinstalled into the glass blocks defining the reaction chamber so that the end of electrode 46 with the membrane 50 and the immobilized sample is positioned on the internal surface of the electrophoretic reaction chamber 20.

The remainder of the sequencing operation is cyclic and includes the following steps:

1. Initial reaction

Isothiocyanate coupling of immobilized protein or peptide amino groups is achieved by electrotransfer of a positively-charged isothiocyanate (e.g. rhodamine B) dissolved in an anhydrous organic solvent (e.g.. 10% n-propanol/90% butyl chloride); to the negative sample electrode 46, the basic conditions required for efficient coupling of isothiocyanates to non-protonated amine groups on the proteins or peptides immobilized at electrode 46 are achieved by the use of an organic solvent soluble acid-base salt (e.g. triethylammonium trifluoroacetate) wherein decomposition to a basic component occurs at the negative sample electrode. The positive electrode in this electrical field (Field 1) is electrode 44. Electrophoretic migration of the pigmented and fluorescent rhodamine ITC can be monitored visually through the transparent glass walls of the cells as can focussing and concentration of the reagent adjacent the electrode 46.

2. Removal of excess reagent

After coupling, unreacted rhodamine B isothiocyanate and its by-products (e.g. thioureas) are electrophoretically transferred to the storage locus 48 at the expanded portion of the reaction chamber using electrode 44 by reversing the polarity of electrodes 46 and 44 (i.e. electrode 46 is now positive with respect to electrode 44).

As in all Edman degradation techniques it is important to achieve a 100% cleavage of each terminal amino acid residue in each cycle. If this is not achieved, the next cycle of coupling and cleavage may be contaminated with terminal amino acids left uncleaved from the previous cycle. In the illustrated embodiment employing HPCE detection of cleaved residues, extremely small numbers of residues are adequate to achieve an unambiguous identification. Accordingly a relatively small coupling efficiency of the charged ITC reagent can be tolerated. If such a low efficiency coupling reagent is used, it is advisable to introduce a high efficiency Edman reagent after coupling of the electrophoretic moiety to couple to and fill any remaining N-terminal residues thereby to ensure 100% cleavage. Accordingly it is desirable to flush the reaction cell with a phenyl-ITC (PITC) reagent of high coupling efficiency after coupling of the rhodamine ITC. As PITC does not bear an electric charge it cannot be electrophoresed and thus is injected by syringe. Removal of unreacted PITC requires flushing of the cell. It is desirable to accomplish this prior to cleavage of reacted ITC derivatives to ensure that penultimate N-terminal residues are not prematurely coupled by PITC although the basic conditions required for such coupling will generally quickly dissipate when electrolysis around the electrode is ceased.

3. Cleavage step

Concomitant with the polarity reversal of electrodes 46 and 44, decomposition occurs at the positively-charged sample electrode 46 as cleavage of the rhodamine B thiocarbamyl amino acid from the immobilized protein or peptide commences. Since this cleavage reaction is relatively slow compared to the electrophoretic movement of unreacted rhodamine B isothiocyanate and its by-products (e.g. thiourea), these latter species will pass electrode 40 before the cleavage reaction has proceeded to any appreciable extent.

4. Transfer of isothiocyanate derivative

Electrode 40 is now made positive with respect to electrode 44, creating an electric field (Field 2) and the electrophoretic migration of the rhodamine B isothiocyanate products continues towards electrode 44. When these products pass electrode 42, this electrode is made positive with respect to electrode 44 (but not as positive as electrode 40) to create an electric field (Field 3) which entraps rhodamine B isothiocyanate near electrode 44 whilst the sample electrode 46 is totally isolated, electrically, from electrodes 44, 42 and 40. At this stage the polarity of electrode 46 is made positive with respect to electrode 38 situated in the injection port 18 of the "capillary electrophoresis" component of the apparatus. The electric field (Field 4) created allows further accumulation of acid and cleavage to occur at the sample electrode 46; the cleaved thiazolinone amino acid derivative (positively charged) migrate through the porous membrane 36 towards electrode 38 in the HPCE sample injection port 18. Separation of the capillary electrophoresis aqueous buffer within the capillary from the anhydrous organic solvent in the reaction chamber is achieved by the hydrophobic membrane 36.

5. Identification of thiazolinone amino acid derivatives

After the completion of the cleavage reaction, the thiazolinone amino acid derivatives which have now accumulated at electrode 38 are identified and quantified with the "capillary electrophoresis" system (for this purpose, electrode 38 is isolated). To further enhance selectivity and sensitivity of detection, the high separation efficiencies of capillary zone electrophoresis can be combined with sensitive fluorescence or mass spectrometric detection (for details said Smith, R. D. et al. (1988) "Capillary Zone Electrophoresis—Mass Spectrometry", Anal. Chem. 60:436–441).

6. Subsequent cleavage cycles

The above-mentioned cycle of the Edman degradation procedure comprising steps 1–5 can be repeated by making the polarity of sample electrode, 46, negative with respect to electrode 44. Alternatively, the reagents and solvent in electrophoretic reaction chamber may be replenished during or at the end of each cycle via the syringes 28. If required, additional reagents for coupling, cleavage or flushing solvents may be introduced into the chamber 20 by the use of one or more of the syringes 28 connected to the input 30.

In the above described embodiment, the positively charged rhodamine derivative of ITC was used and this moiety therefore electrophoretically migrated to the reaction locus. The use of such a positively charged reagent is particularly advantageous in a system such as Edman degradation where the coupling reaction requires basic conditions as in situ generation of the base was also occurring at the reaction locus as an auxiliary salt within the medium, triethylammonium trifluoracetate was being electrolysed.

In an alternative acid catalysed system, a negatively charged group such as fluorescein could be attached to a cleavage reagent and electrophoretically attracted towards a positively charged electrode. At the positive electrode electrolysis of an auxiliary reagent or the medium itself could, simultaneously, be creating acid conditions adjacent the first reagent. Clearly where the reaction between first and additional reagents does not required a pH shift, the medium and any auxiliary reagents would be selected to ensure minimal electrolytic action adjacent the electrode. Use of a fluorescent charged group is convenient as it allows easy optical monitoring of reactant transfer and can also assist in combined fluorescent/CE determinations.

Figure 3:
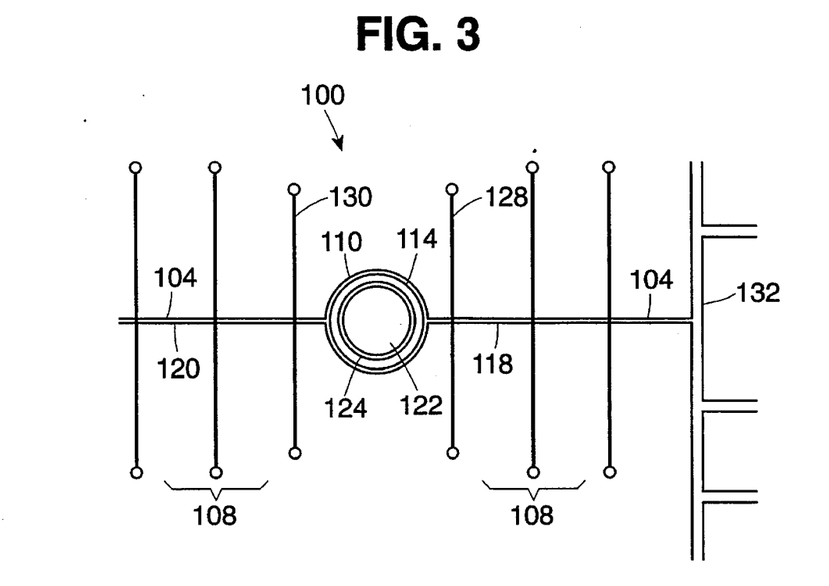
FIG. 3 is a schematic plan view of a second embodiment of reaction apparatus in accordance with the invention.
Figure 4:
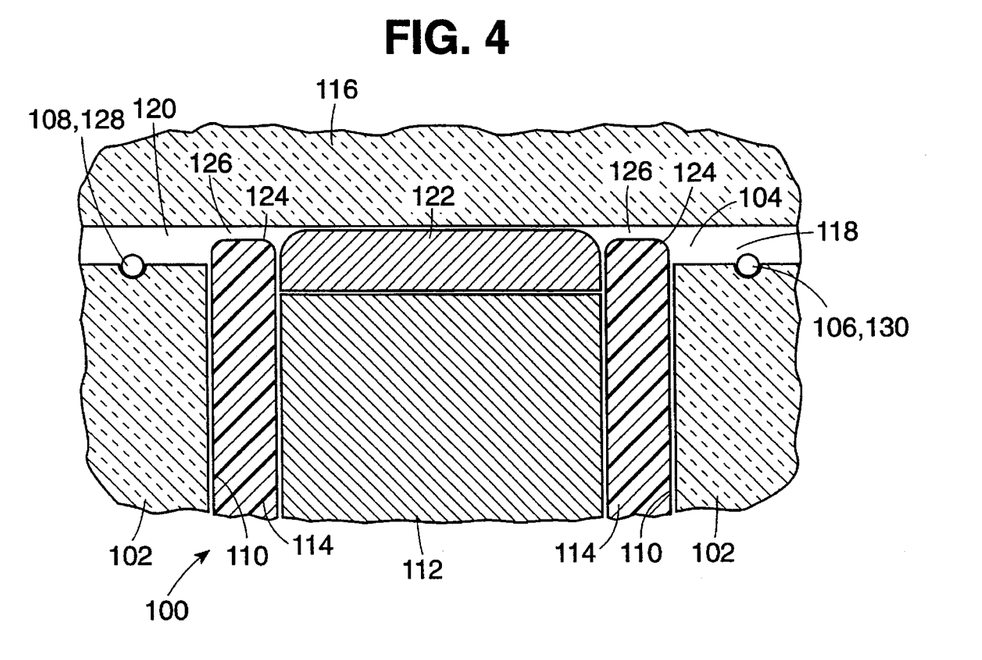
FIG. 4 is a partial sectional side view of the embodiment of FIG. 3.

Referring now to FIGS. 3 and 4 an alternative but generally similar microcell is depicted. In this embodiment the microcell 100, of milled borosilica glass comprises a lower portion 102 having etched therein a longitudinal groove 104 intersected by upstream 106 and downstream 108 sets of three parallel transverse grooves. Bored through the lower portion 102 intermediate the sets 106, 108 of grooves is a vertically extending recess 110 into which is screwed, in use, a 0.8 mm diameter noble metal sample electrode 112 as best seen in FIG. 4. Extending around the electrode is an insulating sheath 114 of PTFE. Sealingly extending over the lower portion 102 is a glass upper portion 116 defining the roof of recess 110 and grooves 104, 106 and 108. The glass upper portion allows direct microscopic observation of the interior of the apparatus and hence allows colorimetric indication of the transfer of reactants. The glass upper cover is omitted in FIG. 3.

In this embodiment recess 110 defines the reaction chamber. Longitudinal groove 104 extending into the chamber defines 0.09 mm diameter upstream 118 and downstream 120 conduit for reagent entry and removal. Extending along each of the transverse grooves in direct electrical communication with the adjacent intersecting conduit 118 or 120 is a respective gold electrode (0.08 mm).

Referring now to FIG. 4, it can be seen that a 0.15 mm deep sample matrix 122 overlies the sample electrode 112. The insulating sheath 114 extends upwardly at reference numeral 124 around the sample matrix although a gap 126 between the sheath and the glass top portion 116 allows entry and exit of reactants from the conduits to the sample matrix. In the described arrangement, the sample matrix 122 of PVDF which except for the insulating sheath, fills recess 110 has a nominal volume 75 nl but with an 80% void volume. The effective reaction chamber in this embodiment is thus 60 nl plus respective volumes of about 1 nl on either side between the recess 110 and the nearest electrode upstream and downstream (respectively 128, 130).

Not depicted in FIGS. 3 and 4 are the downstream analytical device, upstream reagent injection apparatus at manifold 128—Kloehn model 50100 syringe drives, 100 μl syringes, electrical connections between electrodes 112, 118 and 120, power source and microprocessor controller. It is noted however that the spaced electrodes are each independently variable in voltage and polarity. The respective upstream and downstream electrical sets 118 and 120 thus allow for a focusing and electrophoretic movement of charged reagents, somewhat analogous to a peristaltic wave. They can also serve as holding reservoirs as discussed with regard to the embodiment of FIGS. 1 and 2.

Also not indicated in FIGS. 3 and 4 is the amperometric apparatus which measures current flow through the sample electrode 112. Completion of a reaction in the cell is indicated by a plateauing of the current flow in the electrode. This amperometric determination allows easy interface of the cell with a microprocessor controlling the syringe drives responsible for introducing new reactants. The timing of the various steps within a cycle of a sequential step can thus be set according to the reaction kinetics in the particular combination of reactants in the cell.

1. APPARATUS

A simplified version of the apparatus shown in FIG. 2, but lacking the capillary electrophoresis interface, was utilized in this Example. The platinum electrode (46 in FIG. 2) with an affixed PVDF membrane for sample application (50 in FIG. 2) was 5 mm in diameter. One layer of cellulose paper (Whatman 3 MM, 5 mm diam.) was positioned over the PVDF to minimize diffusion of electrolytically generated reagents in the cell. The electrode was insulated (PTFE) so that electric current from the electrode passed through the PVDF. The electrode was positioned in the cell (4-ml glass vessel with a loose-fitting cap), together with a second simple platinum electrode wire. The electrodes were positioned 8 mm apart and connected to a constant power supply.

2. SAMPLE LOADING

The sample (200 picomoles β-lactoglobulin) was immobilized to the PVDF membrane (50), affixed to the sample platinum electrode (46) by passive means. β-lactoglobulin is a 18-kDa protein with the following N-terminal sequence: $H_2N$-Leu-Ile-Val-Thr- (for details see Braunitzer, G. et al. (1972) Z. Physiol. Chemie., 353:832–834).

3. EDMAN DEGRADATION (a) COUPLING The cell was filled with 3.5 ml of butylchloride containing 5% (v/v) phenyl isothiocyanate, 5% (v/v) triethyl ammonium trifluoroacetate and 0.2% (w/v) dithiothreitol. The cell was flushed with argon, heated to 50° C. (air oven) and connected to a constant power supply (200 μA, 20–30 V) for 60 mins with the sample electrode (46) negative. The sample electrode was then removed from the cell, briefly washed (30 sec) with 0.5 ml ethylacetate and returned to the cell for the cleavage reaction.

(b) CLEAVAGE The cell was filled with 3.5 ml butylchloride containing 10% (v/v) trifluoroacetic acid and 0.2%

(w/v) dithiothreitol, heated to 50° C. (air oven) and connected (sample electrode, positive) to the power supply (36 V, 50 μA) for 30 mins. The sample electrode was then removed from the cell.

4. DETERMINATION OF REMAINING N-TERMINAL RESIDUES

The PVDF membrane was removed from the sample electrode, washed with 0.5 ml ethyl acetate, and placed in the sample cartridge of an Applied Biosystems Sequencer (model 470A) equipped with an on-line phenylthiohydantoin (PTH)—amino acid analyzer. Sequence analysis of the N-terminal residues of the β-lactoglobulin remaining on the membrane was performed using regular Applied Biosystems cycles and program O3RTST. The sequencing results are shown in FIG. 5.

Figure 5:
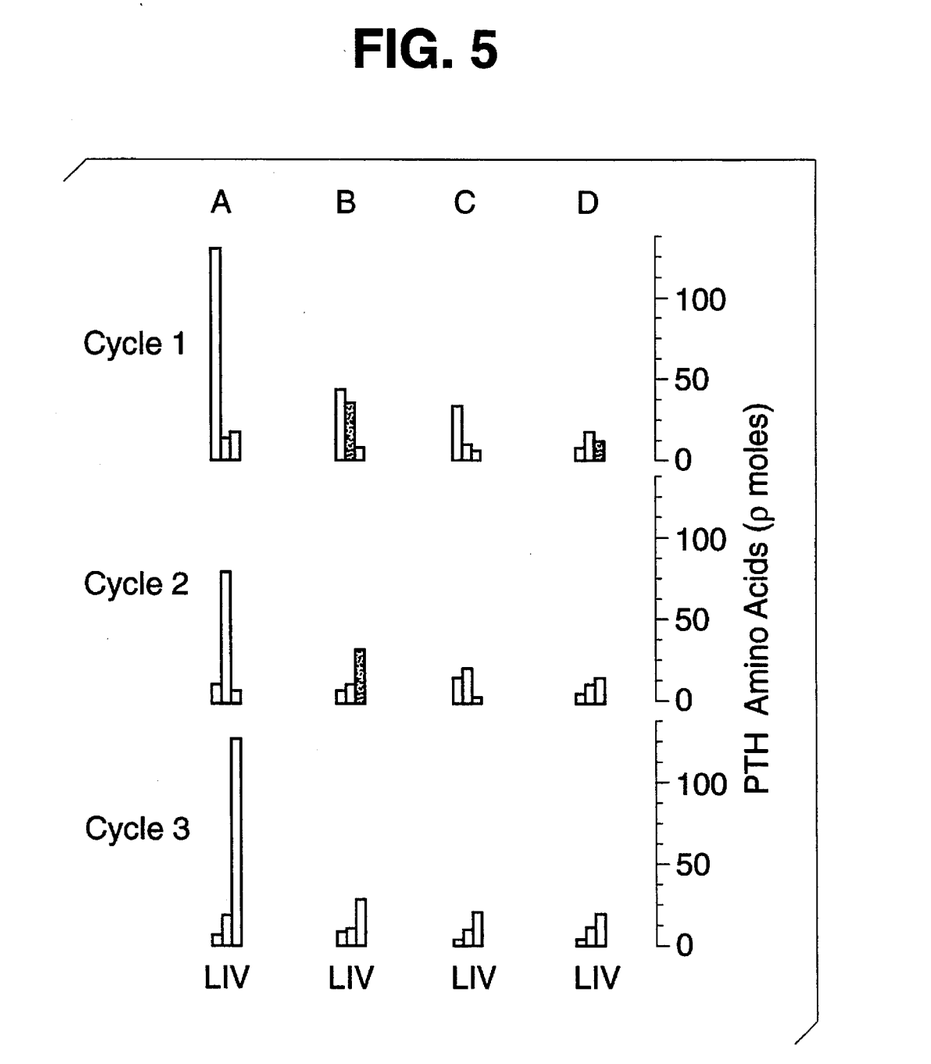
FIG. 5 is a graph depicting amino acid determination data of experiments A to D in Example 1.

Legend To FIG. 5:

A Control (β-lactoglobulin sequence was determined directly in 470A i.e. omitting step 3)

B One Edman degradation cycle was performed including electrolytic generation of The basic and acidic conditions required for coupling and cleavage and the remaining N-terminal residues sequenced in 470A C Control for 'B' (i.e., identical treatment as in B, but no electrolysis)

D Two Edman degradation cycles were performed electrolytically and the remaining N-terminal residues sequenced in 470A Note:

(1) One letter notation used for amino acids i.e., L, leucine; I, isoleucine and V, valine.

(2) Cycle 1, 2 and 3 in the leftmost legend corresponds to the first, second and third cycles of the 470A sequencing of the N-terminal residues remaining on the respective membrane.

5. COMMENTS (a) In Expt B: The presence of Ile in cycle 1, Val in cycle 2 (Thr in cycle 3 was too low to be detected) is clear evidence that the N-terminal leucine has been removed by the electrolytic coupling and cleavage procedure described in 3(a) and 3(b).

(b) confirmation that the removal of N-terminal leucine was due to the electrolytic process and not just due to passive exposure to the reagents is provided by the data in Expt C i.e., Compare Ile levels in cycle 1 (Val levels in cycle 2) in Expts B and C. In Expt C, β-lactoglobulin was exposed to the same regimen of chemicals as in B for the same time and temperature but no electrolysis was performed.

(c) In Expt D: The presence of increased levels of Val in cycle 1 is indicative of two successful cycles of Edman degradation having been performed by the electrolytic procedure described in 3(a) and 3(b) (i.e., compare Val level in Expt D with those in B and C—cycle 1).

(d) In the above described experiments NO attempt has been made to optimize the kinetics/chemistry of the coupling/cleavage processes.

EXAMPLE 2

This Example is similar in intent to Example 1 but performed on the micro/nano scale apparatus described by reference to FIGS. 3 and 4. The Example included the following experiments:

(A) Control

Summary

β-lactoglobulin is adsorbed to sample matrix and then sequenced using a standard ABI 420 Sequencer.

Procedure

β-lactoglobulin adsorbed onto PVDF disc 0.8 mm diameter 0.15 mm thick. PVDF discs (=50) prewetted in acetonitrile then immersed in 1 ml 10% acetonitrile 10 mgm β-lactoglobulin for 1 hour at 20° C. Protein solution poured off the discs, washed 10 times (=5 ml) 10% acetonitrile. Discs washed 10 times in water then dried in freeze dryer stored under argon at −20° C. One disc placed into ABI 470 Sequencer with preconditioned polybrene glass disc. Normal PTH cycles.

(B) Example of Electrolytic Coupling

Summary

β-lactoglobulin is adsorbed to sample matrix and the matrix is disposed in the microcell of FIGS. 3 and 4. PITC Edman reagent is introduced to the microcell where basic conditions are electrolytically generated in situ. The sample matrix is then sequenced with ABI 470.

Procedure

β-lactoglobulin PVDF disc prepared as in (A) is placed in the microcell. PITC Edman reagent is injected as 5% PITC, 5% TEAFTA (triethylammonium trifluoroacetate) and 0.01% DTT in butyl chloride. The sample electrode is charged negatively, with both proximal electrodes 128, 130 positive, 15 volts 0.6 μA to achieve coupling of the PITC with the N-terminal amino acid. Charge is maintained for 30 minutes while the temperature is kept at 50° C. The sample disc is washed with 100 μl butyl chloride then removed from microcell and placed into ABI 470 Sequencer with preconditioned polybrene disc. Program started at O3CPTH step 15 (no coupling in first cycle, only washes and cleavage).

(C) Example of Electrolytic Coupling and Cleavage

Summary

β-lactoglobulin PVDF disc placed in microcell, PITC introduced and electrolytically coupled as (B) above then polarity reversal to produce conditions for cleavage of terminal amino acid. The sample matrix is then sequenced with ABI 470.

Procedure

β-lactoglobulin PVDF disc prepared as in (A), placed into microcell, coupled with PITC as detailed for (B), washed with 100 μl butyl chloride then cleaved in microcell as follows: 10% trifluoroacetate, 0.01% DTT in butyl chloride introduced to the cell. Sample electrode made positive, both proximal electrodes 128, 130 negative. Temperature maintained at 50° C. 15 minutes of 15 volts, 0.6 μA. Sample disc washed with 100 μl butyl chloride then removed from microcell and placed into ABI Sequencer with a preconditioned polybrene disc (normal O3CPTH cycles used).

(D) Control for (C)

Summary

PITC introduced, but basic and acidic conditions not electrolytically generated, sample matrix sequenced with ABI 470.

Procedure

Exactly the same as (C) except no electrical current used in the microcell. Same coupling and cleavage reagents, time and temperature.

(E) Example of Electrophoretic ITC Introduction and Electrolytic Coupling and Cleavage Summary β-lactoglobulin PVDF disc placed in microcell, rhodamine ITC electrophoretically focused onto the sample matrix. Basic conditions electrolytically generated to promote coupling then acid conditions to achieve cleavage. Sample matrix then sequenced with ABI 470.

Procedure

β-lactoglobulin PVDF disc prepared as in (A) placed into microcell. Coupling achieved by injecting 10 mg rhodamine ITC, 5% TEAFTA, 0.01% DTT in 5 ml butyl chloride. Sample electrode held negative 15 volts, 0.7 µA for 30 minutes with both proximal electrodes positive. Temperature maintained at 50° C. Cell washed with 100 µl butyl chloride then cleaved as described for (C). Cell washed with 100 µl butyl chloride. Disc removed from microcell and placed into ABI 470 Sequencer with preconditioned polybrene disc (normal O3CPTH cycles).

Figure 6:
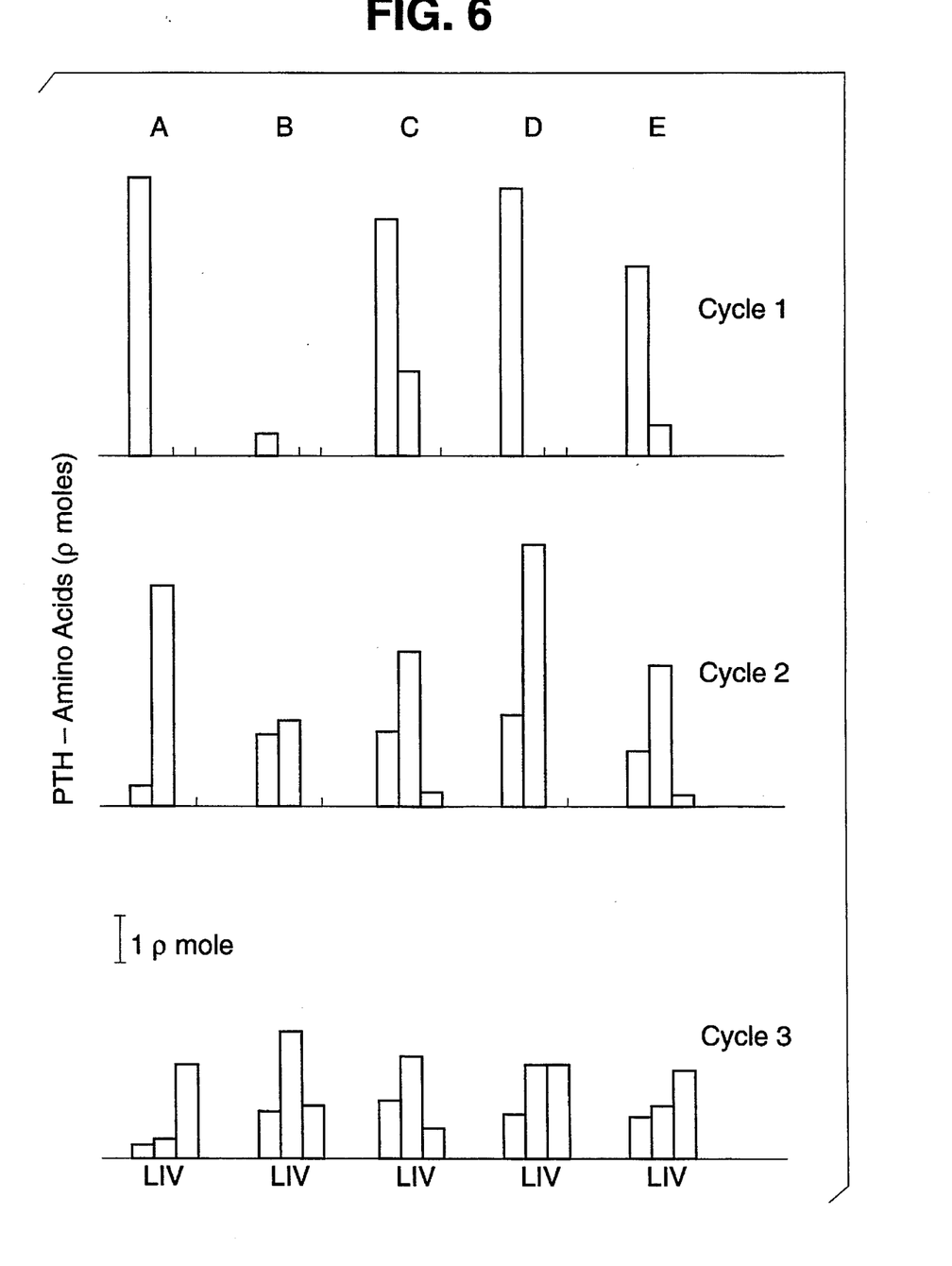
FIG. 6 is a graph depicting amino acid determination data of experiments A to E in Example 2.

The data from each of experiments A to E above are depicted on FIG. 6, expressed as picomoles, PTH-amino acids released per cycle (1 letter amino acid codes). Three cycles of the ABI 470 were undertaken (i.e. the three N-terminal amino acids of the β-lactoglobulin remaining on the sample matrix were identified).

Referring to FIG. 6, reading control (A) downwards through the three cycles, the N-terminal sequence is clearly Leu-Ile-Val.

In experiment (B), the presence of Leu at cycle 1 indicates coupling (but not cleavage) of PITC to the β-lactoglobulin. At cycle 3 however it is apparent that all three amino acids survived the initial electrolytic coupling reaction of PITC to L.

In experiment (C), (electrolytic coupling and cleavage), the thing to note is the presence of a relatively large Ile figure in the first cycle. (The Leu reading merely indicates non optimal cleavage of this experimental system.) The presence of an Ile reading in the first cycle of the remaining amino acids on the sample matrix clearly shows that cleavage of the end terminal L has been effective. Similarly the Val reading in the second cycle, shows that Ile was the terminal amino acid.

Experiment (D), the control for experiment (C), indicates that without energizing of the electrode, truncation of the terminal amino acids does not take place.

In experiment (E), as with (C) above, The presence of Ile in the first cycle and Val in the second cycle indicates that the electrophoretic/electrolytic coupling/cleavage successfully removed the terminal amino acid.

Although the invention has been illustrated by reference to the Edman degradation sequencing of a protein, the application of electrophoretic transfers of a chemical reactant to or from an immobilized first reactant and/or electrolytic activation of reactants may be applicable to other sequencing and/or sequential chemical reactions, such as the construction of macromolecules. Furthermore, apparatus in accordance with the invention may have a plurality of spaced storage loci by providing a plurality of electrodes spaced from the reaction locus and under the control of appropriate electric voltages.

We claim:

1. A method for conducting a chemical reaction, wherein said method comprises, immobilizing a first reactant at the reaction locus, introducing an additional reactant to the reaction locus, allowing a reaction between the first and second reactants to produce a reaction by-product in an anhydrous medium, if the by-product is not charged, imparting an electric charge to the reaction by-product and electrophoretically removing the reaction by-product from the reaction locus, and further comprising an electrolytic activation step comprising electrolytically activating a reaction between the first and additional reactants and removing remaining additional reactant and/or a reaction by-product from the reaction locus.

2. A method for conducting a chemical reaction, wherein said method comprises, immobilizing a first reactant at a reaction locus, introducing an additional reactant to the reaction locus, allowing a reaction between the first and second reactants to produce a reaction by-product in an anhydrous medium, if the by-product is not charged, imparting an electric charge to the reaction by-product, and electrophoretically removing the reaction by-product from the reaction locus, and wherein the by-product immediately after the reaction is not charged and wherein a charged surfactant is introduced to the reactant locus to impart a charge to the by-product.

3. A method of conducting a chemical reaction, the method comprising, immobilizing a first reactant at a reaction locus, electrophoretically introducing to the reaction locus at least one charged, additional reactant in an anhydrous medium, and after the reaction between the first and additional reactants removing the remaining additional reactant and/or a reaction by-product of the reaction from the reaction locus, and wherein additional reactant remaining from the reaction is electrophoretically removed from the reaction locus by energizing an electrode remote from the reaction locus with an electric charge of greater magnitude than that of the reaction locus, and further wherein the polarity of the electrode adjacent the reaction locus is reversed to enable the remote electrode to bear the greater magnitude of electric charge.

4. A method of conducting a chemical reaction, the method comprising immobilizing a first reactant at a reaction locus, electrophoretically introducing to the reaction locus at least one charged additional reactant in an anhydrous medium, and after reaction between the first and additional reactants removing the remaining additional reactant and/or a reaction by-product of the reaction from the reaction locus, and wherein additional reactant remaining from the reaction is electrophoretically removed from the reaction locus by energizing an electrode remote from the reaction locus with an electric charge of greater magnitude than that of the reaction locus, and further wherein the remote electrode defines a storage locus for additional reactant and wherein additional reactant can be electrophoretically reintroduced to the reaction locus.

* * * * *